(12) United States Patent
Alzain

(10) Patent No.: US 10,070,946 B1
(45) Date of Patent: Sep. 11, 2018

(54) DEVICE FOR RECORDING VERTICAL AND CENTRIC OCCLUSION POSITIONS OF EDENTULOUS JAWS

(71) Applicant: KING SAUD UNIVERSITY, Riyadh (SA)

(72) Inventor: Sahar Asaad Alzain, Riyadh (SA)

(73) Assignee: KING SAUD UNIVERSITY, Riyadh (SA)

(*) Notice: Subject to any disclaimer, the term of this patent is extended or adjusted under 35 U.S.C. 154(b) by 0 days.

(21) Appl. No.: 15/833,868

(22) Filed: Dec. 6, 2017

(51) Int. Cl.
  *A61C 11/08* (2006.01)
  *A61C 19/05* (2006.01)
  *A61C 19/045* (2006.01)

(52) U.S. Cl.
  CPC .............. *A61C 11/08* (2013.01); *A61C 19/05* (2013.01); *A61C 19/045* (2013.01)

(58) Field of Classification Search
  CPC ........... A61C 11/08; A61C 11/02; A61C 9/00; A61C 19/05; A61C 19/045
  USPC ........................................ 433/60, 68, 70, 71
  See application file for complete search history.

(56) References Cited

U.S. PATENT DOCUMENTS

| | | | | |
|---|---|---|---|---|
| 1,976,045 A | * | 10/1934 | Sorenson | A61C 19/00 33/513 |
| 3,381,377 A | * | 5/1968 | Grayson | A61C 19/05 433/27 |
| 4,265,620 A | * | 5/1981 | Moro | A61C 19/045 433/54 |
| 4,504,226 A | | 3/1985 | Gordon | |
| 5,266,031 A | | 11/1993 | Marigza | |
| 6,109,917 A | * | 8/2000 | Lee | A61C 19/045 433/68 |
| 6,206,693 B1 | | 3/2001 | Hultgren | |
| 6,582,931 B1 | * | 6/2003 | Kois | A61C 11/003 33/513 |
| 7,220,123 B1 | | 5/2007 | Karapetyan | |
| 9,788,919 B1 | | 10/2017 | Alotaibi et al. | |
| 2003/0138755 A1 | * | 7/2003 | Tremont | A61C 19/045 433/68 |
| 2012/0164595 A1 | * | 6/2012 | Su | A61C 11/08 433/54 |
| 2012/0295219 A1 | * | 11/2012 | Monteiro Geras | A61C 11/08 433/55 |
| 2013/0323676 A1 | * | 12/2013 | Abdala Pastor | A61C 11/08 433/60 |

(Continued)

*Primary Examiner* — Nicholas Lucchesi
(74) *Attorney, Agent, or Firm* — Richard C. Litman

(57) ABSTRACT

The device for recording vertical and centric occlusion positions of edentulous jaws is a tool which allows a dental practitioner to maintain maxillary and mandibular record bases (and their respective wax rims) in their respective vertical and centric occlusion positions during transfer of the maxillary and mandibular record bases to a conventional dental articulator. A pair of telescopically adjustable rods are provided for measuring the vertical occlusion position of the patient's edentulous jaws. Each of the telescopically adjustable rods has a selectively adjustable and lockable height, with the opposed ends thereof being releasably secured to the maxillary and mandibular record bases, respectively. The telescopically adjustable rods are also horizontally adjustable with respect to the maxillary and mandibular record bases, allowing the centric occlusion position of the patient's edentulous jaws to be recorded.

10 Claims, 2 Drawing Sheets

(56) References Cited

U.S. PATENT DOCUMENTS

2014/0234797 A1* 8/2014 Elnajjar ................ A61C 11/08
                                                    433/60
2017/0128180 A1   5/2017 Palaskar

* cited by examiner

DEVICE FOR RECORDING VERTICAL AND CENTRIC OCCLUSION POSITIONS OF EDENTULOUS JAWS

BACKGROUND

1. Field

The disclosure of the present patent application relates to the making of dental casts and the like, and particularly to a device for recording vertical and centric occlusion positions of edentulous jaws of patient during the process of making dental casts.

2. Description of the Related Art

In the making of dentures, record bases and wax rims are used for recording the postural position of the mandible in relation to the maxilla, allowing for arrangement of the denture teeth in their correct occlusal relationship. The contoured wax rims, which are respectively mounted on maxillary and mandibular record bases, are used as an aid in developing the proper contour of the lips and cheeks, developing the plane of occlusion, and determining the proper position of the incisal edges of the maxillary anterior teeth. After recordation via impressions made in the wax rims, and following casting of the denture teeth, the maxillary and mandibular record bases are moved to a fixation tool, referred to as an articulator, which is an instrument which simulates the temporomandibular joints and jaw members. The maxillary and mandibular casts are attached to the articulator to simulate some or all mandibular movement of the patient. Unfortunately, during transfer to the articulator, it is difficult to maintain the vertical and/or centric occlusion positions between the maxillary and mandibular casts. Thus, a device for recording vertical and centric occlusion positions of edentulous jaws solving the aforementioned problems is desired.

SUMMARY

The device for recording vertical and centric occlusion positions of edentulous jaws is a tool which allows a dental practitioner to maintain maxillary and mandibular record bases (and their respective wax rims) in their respective vertical and centric occlusion positions during transfer of the maxillary and mandibular record bases to a conventional dental articulator. The device for recording vertical and centric occlusion positions of edentulous jaws includes both a maxillary record base, having a pair of maxillary threaded shafts secured thereto and projecting outwardly therefrom, and a mandibular record base, also having a pair of mandibular threaded shafts secured thereto and projecting outwardly therefrom. A pair of maxillary tubes, each having opposed first and second ends and a threaded interior surface, are provided such that the pair of maxillary threaded shafts may be respectively selectively and adjustably received by the respective first ends of the pair of maxillary tubes. Similarly, a pair of mandibular tubes, each having opposed first and second ends and a threaded interior surface, are provided such that the pair of mandibular threaded shafts may be respectively selectively and adjustably received by the respective first ends of the pair of mandibular tubes.

A pair of telescopically adjustable rods are further provided, with each having opposed maxillary and mandibular ends, with a maxillary passage being formed through the maxillary end of each of the telescopically adjustable rods, and a mandibular passage being formed through the mandibular end of each of the telescopically adjustable rods. The pair of maxillary tubes are respectively slidably received within the maxillary passages of the pair of telescopically adjustable rods, and the pair of mandibular tubes are respectively slidably received within the mandibular passages of the pair of telescopically adjustable rods.

A pair of maxillary screws, each having a head and a threaded shaft, are provided such that the threaded shafts of the pair of maxillary screws may be respectively selectively and adjustably received by the respective second ends of the pair of maxillary tubes. Similarly, a pair of mandibular screws are also provided, each having a head and a threaded shaft, such that the threaded shafts of the pair of mandibular screws may be respectively selectively and adjustably received by the respective second ends of the pair of mandibular tubes. The vertical position of each of the telescopically adjustable rods is preferably selectively lockable through the usage of a respective pair of locking screws or the like.

In use, each of the maxillary and mandibular record bases receives a respective wax rim in a conventional manner. The maxillary and mandibular record bases, and their respective wax rims, are then inserted in the patient's mouth in the conventional manner. In order to record the vertical and centric occlusion positions of the patient's edentulous jaws, the vertical height of the pair of telescopically adjustable rods (representing the patient's vertical occlusion position) is locked in place by the pair of locking screws. The centric occlusion position is recorded by horizontally sliding the telescopically adjustable rods, with the pair of maxillary tubes being slidable within the maxillary passages of the pair of telescopically adjustable rods, and the pair of mandibular tubes being slidable within the mandibular passages of the pair of telescopically adjustable rods. It should be understood that the pair of maxillary tubes and the pair of mandibular tubes are stationary with respect to the maxillary and mandibular record bases, respectively, such that the telescopically adjustable rods are horizontally adjustable with respect to the maxillary and mandibular record bases. A temporary centric position is recorded by the horizontal positioning of the telescopically adjustable rods, with their horizontal positioning being limited through the respective selective tightening of the maxillary and mandibular screws. With the vertical and centric occlusion positions recorded and fixed, the device may then be transferred to a conventional dental articulator for mounting of casts by unscrewing the maxillary and mandibular tubes from the respective maxillary and mandibular threaded shafts.

These and other features of the present invention will become readily apparent upon further review of the following specification.

BRIEF DESCRIPTION OF THE DRAWINGS

Similar reference characters denote corresponding features consistently throughout the attached drawings.

DETAILED DESCRIPTION OF THE PREFERRED EMBODIMENTS

Figure 1:
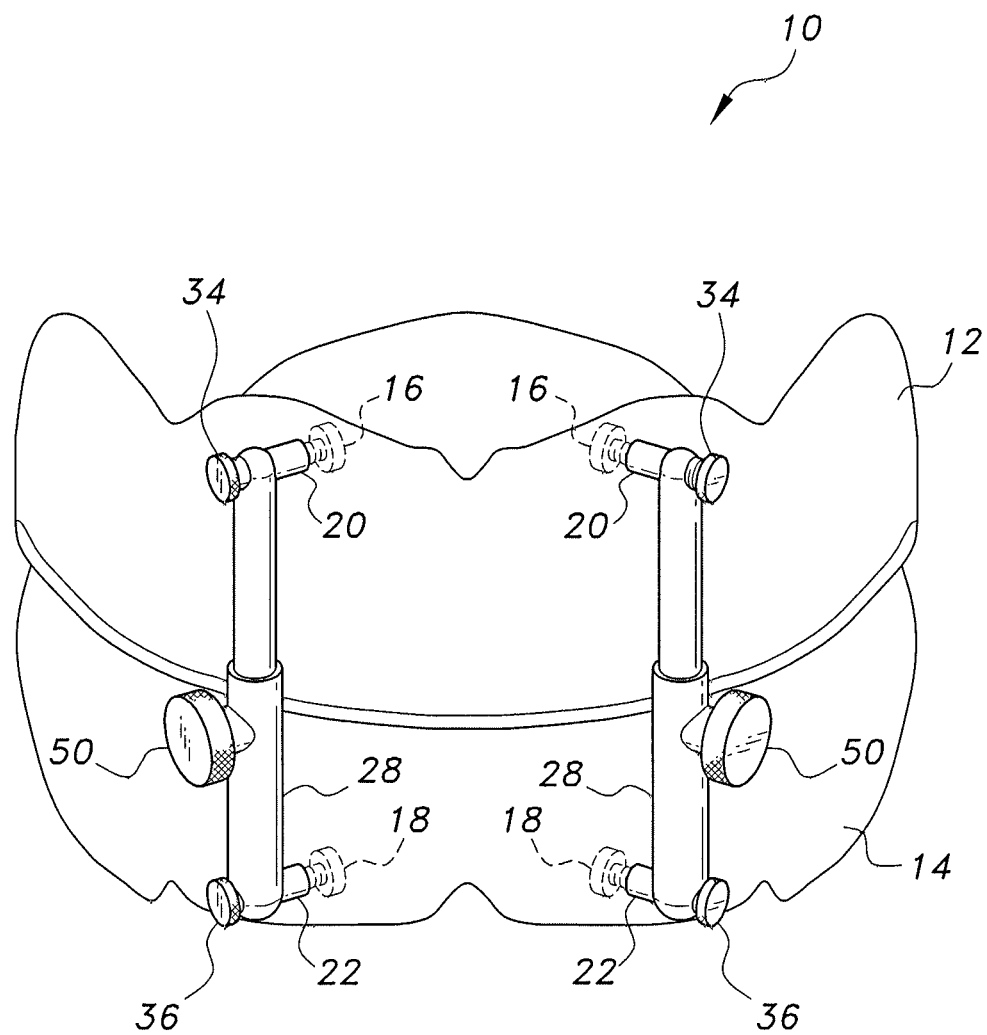
FIG. 1 is a perspective view of a device for recording vertical and centric occlusion positions of edentulous jaws.
Figure 2:
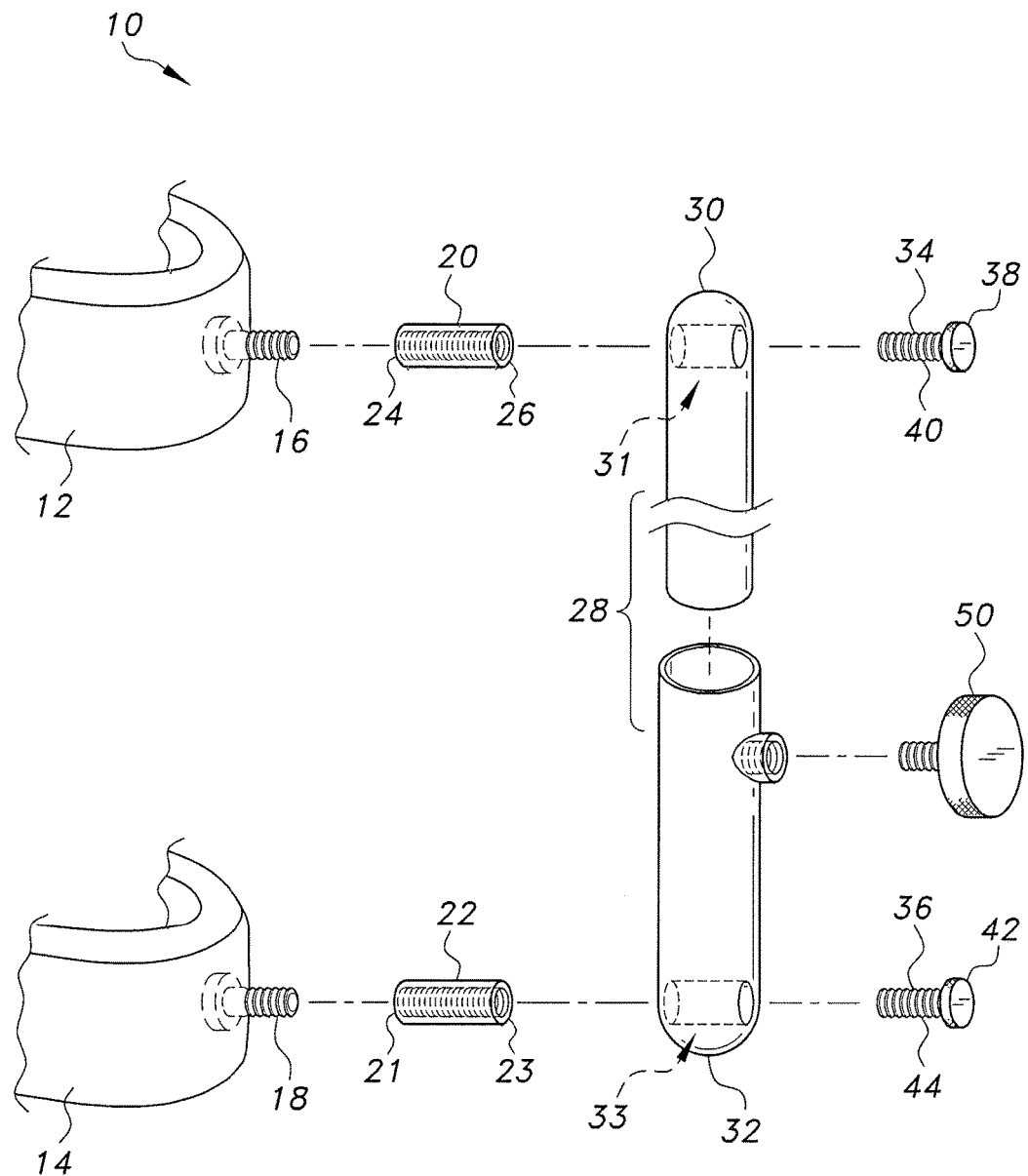
FIG. 2 is a side exploded view of the device for recording vertical and centric occlusion positions of edentulous jaws.

The device for recording vertical and centric occlusion positions of edentulous jaws 10 is a tool which allows a dental practitioner to maintain maxillary and mandibular record bases (and their respective wax rims) in their respective vertical and centric occlusion positions during transfer of the maxillary and mandibular record bases to a conventional dental articulator. As shown in FIGS. 1 and 2, the device for recording vertical and centric occlusion positions of edentulous jaws 10 includes both a maxillary record base 12, having a pair of maxillary threaded shafts 16 secured thereto and projecting outwardly therefrom, and a mandibular record base 14, also having a pair of mandibular threaded shafts 18 secured thereto and projecting outwardly therefrom. As shown in FIG. 2, in order to manufacture the maxillary record base 12 and the mandibular record base 14 with respective pairs of threaded shafts 16, 18, each of the record bases 12, 14 may be molded in a conventional manner but each with a pair of threaded screws or bolts embedded therein, such that the head of each threaded screw or bolt is used to anchor the corresponding shaft 16, 18 in place. Maxillary and mandibular record bases 12, 14 are preferably constructed in a manner similar to conventional dental record bases, and are formed from acrylic or the like.

A pair of maxillary tubes 20, each having opposed first and second ends 24, 26, respectively, and a threaded interior surface, are provided such that the pair of maxillary threaded shafts 16 may be respectively selectively and adjustably received by the respective first ends 24 of the pair of maxillary tubes 20. Similarly, a pair of mandibular tubes 22, each having opposed first and second ends 21, 23, respectively, and a threaded interior surface, are provided such that the pair of mandibular threaded shafts 18 may be respectively selectively and adjustably received by the respective first ends 21 of the pair of mandibular tubes 22. For conventional dentistry, each of the maxillary and mandibular threaded shafts 16, 18 may have a length of approximately 5 mm, for example. An exemplary thickness of a corresponding head of the embedded threaded screw or bolt (as shown in FIG. 2) may be on the order of 2 mm. Each of the maxillary and mandibular threaded shafts 16, 18 may have a diameter of approximately 4 mm, for example, with the interior of maxillary and mandibular tubes 20, 22 having a corresponding diameter. Each of the maxillary and mandibular tubes 20, 22, respectively, may have a length of approximately 15 mm. As shown, the maxillary and mandibular threaded shafts 16, 18 are positioned mesial with respect to the maxillary and mandibular canines of the patient, respectively.

A pair of telescopically adjustable rods 28 are further provided, with each having opposed maxillary and mandibular ends 30, 32, respectively. A maxillary passage 31 is formed through the maxillary end 30 of each of the telescopically adjustable rods 28, and a mandibular passage 33 is similarly formed through the mandibular end 32 of each of the telescopically adjustable rods 28. The pair of maxillary tubes 20 are respectively slidably received within the maxillary passages 31 of the pair of telescopically adjustable rods 28, and the pair of mandibular tubes 22 are respectively slidably received within the mandibular passages 32 of the pair of telescopically adjustable rods 28. It should be understood that any suitable type of telescopic or vertically adjustable rods may be used. In the relatively simple example of FIGS. 1 and 2, in which a conventional two-piece telescopic rod 28 is utilized, the larger diameter tube (in the example of FIGS. 1 and 2, the lower, or mandibular, tube) may have an outer diameter of approximately 6 mm and a length of approximately 40 mm, and the smaller diameter tube (in the example of FIGS. 1 and 2, the upper, or maxillary, tube), may have an outer diameter of approximately 5 mm and a length of approximately 60 mm.

A pair of maxillary screws 34, each having a head 38 and a threaded shaft 40, are provided such that the threaded shafts 40 thereof may be respectively selectively and adjustably received by the respective second ends 26 of the pair of maxillary tubes 20. Similarly, a pair of mandibular screws 36 are also provided, each having a head 42 and a threaded shaft 44, such that the threaded shafts 44 thereof may be respectively selectively and adjustably received by the respective second ends 23 of the pair of mandibular tubes 22. The vertical position of each of the telescopically adjustable rods 28 is preferably selectively lockable through the usage of a respective pair of locking screws 50 or the like, as shown in FIG. 1. Preferably, device 10, with the exception of the maxillary and mandibular record bases 12, 14, is made from stainless steel or a similar material which can be sterilized in an autoclave for re-use.

In use, each of the maxillary and mandibular record bases 12, 14, respectively, receives a respective wax rim in a conventional manner. The maxillary and mandibular record bases 12, 14, and their respective wax rims, are then inserted in the patient's mouth in the conventional manner. In order to record the vertical and centric occlusion positions of the patient's edentulous jaws, the vertical height of the pair of telescopically adjustable rods 28 (representing the patient's vertical occlusion position) is locked in place by the pair of locking screws 50. The centric occlusion position is recorded by horizontally sliding the telescopically adjustable rods 28, with the pair of maxillary tubes 20 being slidable within the maxillary passages 31 of the pair of telescopically adjustable rods 28, and the pair of mandibular tubes 22 being slidable within the mandibular passages 33 of the pair of telescopically adjustable rods 28. It should be understood that the pair of maxillary tubes 20 and the pair of mandibular tubes 22 are stationary with respect to the maxillary and mandibular record bases 12, 14, respectively, such that the telescopically adjustable rods 28 are horizontally adjustable with respect to the maxillary and mandibular record bases 12, 14. A temporary centric position is recorded by the horizontal positioning of the telescopically adjustable rods 28 on the maxillary tubes 20 and mandibular tubes 22, with their horizontal positioning being limited through the respective selective tightening of the maxillary and mandibular screws 34, 36, respectively. With the vertical and centric occlusion positions recorded and fixed, the device 10 may then be transferred to a conventional dental articulator for mounting of casts by unscrewing the maxillary and mandibular tubes 20, 22 from the respective maxillary and mandibular threaded shafts 16, 18.

It is to be understood that the device for recording vertical and centric occlusion positions of edentulous jaws is not limited to the specific embodiments described above, but encompasses any and all embodiments within the scope of the generic language of the following claims enabled by the embodiments described herein, or otherwise shown in the drawings or described above in terms sufficient to enable one of ordinary skill in the art to make and use the claimed subject matter.

I claim:
1. A device for recording vertical and centric occlusion positions of edentulous jaws, comprising:
   a maxillary record base having a pair of maxillary threaded shafts secured thereto and projecting outwardly therefrom;

a mandibular record base having a pair of mandibular threaded shafts secured thereto and projecting outwardly therefrom;

a pair of maxillary tubes, each having opposed first and second ends and a threaded interior surface, the pair of maxillary threaded shafts being respectively, selectively adjustably received by the respective first ends of the pair of maxillary tubes;

a pair of mandibular tubes, each having opposed first and second ends and a threaded interior surface, the pair of mandibular threaded shafts being respectively, selectively adjustably received by the respective first ends of the pair of mandibular tubes;

a pair of telescopically adjustable rods, each having opposed maxillary and mandibular ends, a maxillary passage being formed through the maxillary end of each of the telescopically adjustable rods, and a mandibular passage being formed through the mandibular end of each of the telescopically adjustable rods, wherein the pair of maxillary tubes are respectively slidably received within the maxillary passages of the pair of telescopically adjustable rods, and the pair of mandibular tubes are respectively slidably received within the mandibular passages of the pair of telescopically adjustable rods;

a pair of maxillary screws, each having a head and a threaded shaft, the threaded shafts of the pair of maxillary screws being respectively, selectively adjustably received by the respective second ends of the pair of maxillary tubes; and a pair of mandibular screws, each having a head and a threaded shaft, the threaded shafts of the pair of mandibular screws being respectively, selectively adjustably received by the respective second ends of the pair of mandibular tubes.

2. The device for recording vertical and centric occlusion positions of edentulous jaws as recited in claim 1, wherein each of the telescopically adjustable rods is selectively lockable.

3. The device for recording vertical and centric occlusion positions of edentulous jaws as recited in claim 1, wherein the maxillary threaded shafts and the mandibular threaded shafts have a length of about 5 mm.

4. The device for recording vertical and centric occlusion positions of edentulous jaws as recited in claim 1, wherein the maxillary threaded shafts and the mandibular threaded shafts have a diameter of about 4 mm.

5. The device for recording vertical and centric occlusion positions of edentulous jaws as recited in claim 1, wherein the maxillary tubes and the mandibular tubes have a length of about 15 mm.

6. A device for recording vertical and centric occlusion positions of edentulous jaws, comprising:

a maxillary record base having at least one maxillary threaded shaft secured thereto and projecting outwardly therefrom;

a mandibular record base having at least one mandibular threaded shaft secured thereto and projecting outwardly therefrom;

at least one maxillary tube having opposed first and second ends and a threaded interior surface, the at least one maxillary threaded shaft being selectively adjustably received by the first end of the at least one maxillary tube;

at least one mandibular tube having first and second ends and a threaded interior surface, the at least one mandibular threaded shaft being selectively adjustably received by the first end of the mandibular tube;

at least one telescopically adjustable rod having opposed maxillary and mandibular ends, a maxillary passage being formed through the maxillary end of the at least one telescopically adjustable rod, and a mandibular passage being formed through the mandibular end of the at least one telescopically adjustable rod, wherein the at least one maxillary tube is slidably received within the maxillary passage of the at least one telescopically adjustable rod, and the at least one mandibular tube is slidably received within the mandibular passage of the at least one telescopically adjustable rod;

at least one maxillary screw having a head and a threaded shaft, the threaded shaft of the at least one maxillary screw being selectively adjustably received by the second end of the at least one maxillary tube; and at least one mandibular screw having a head and a threaded shaft, the threaded shaft of the at least one mandibular screw being selectively adjustably received by the second end of the at least one mandibular tube.

7. The device for recording vertical and centric occlusion positions of edentulous jaws as recited in claim 6, wherein the at least one telescopically adjustable rod is selectively lockable.

8. The device for recording vertical and centric occlusion positions of edentulous jaws as recited in claim 6, wherein the at least one maxillary threaded shaft and the at least one mandibular threaded shaft has a length of about 5 mm.

9. The device for recording vertical and centric occlusion positions of edentulous jaws as recited in claim 6, wherein the at least one maxillary threaded shaft and the at least one mandibular threaded shaft has a diameter of about 4 mm.

10. The device for recording vertical and centric occlusion positions of edentulous jaws as recited in claim 6, wherein the at least one maxillary tube and the at least one mandibular tube has a length of about 15 mm.

* * * * *